United States Patent
Korkala et al.

(10) Patent No.: US 10,182,737 B2
(45) Date of Patent: Jan. 22, 2019

(54) EMI PROTECTION FOR PHYSIOLOGICAL MEASUREMENTS

(71) Applicant: POLAR ELECTRO OY, Kempele (FI)

(72) Inventors: Seppo Korkala, Kempele (FI); Kaisa Lämsä, Kempele (FI); Elias Pekonen, Oulu (FI)

(73) Assignee: Polar Electro Oy, Kempele (FI)

( * ) Notice: Subject to any disclaimer, the term of this patent is extended or adjusted under 35 U.S.C. 154(b) by 0 days.

(21) Appl. No.: 15/707,530

(22) Filed: Sep. 18, 2017

(65) Prior Publication Data

US 2018/0220918 A1 Aug. 9, 2018

(30) Foreign Application Priority Data

Feb. 6, 2017 (EP) .................... 17154739

(51) Int. Cl.
*A61B 5/0408* (2006.01)
*A61B 5/0478* (2006.01)
(Continued)

(52) U.S. Cl.
CPC .......... *A61B 5/0478* (2013.01); *A61B 5/0245* (2013.01); *A61B 5/0408* (2013.01);
(Continued)

(58) Field of Classification Search
CPC .......... A61B 5/6804–5/6807; A61B 2562/182; A61B 5/04; A61B 5/04085; A61B 5/0424; A61B 5/0478; A61B 5/0492
(Continued)

(56) References Cited

U.S. PATENT DOCUMENTS

| 4,478,225 A | 10/1984 | Ewing | |
| 4,763,660 A * | 8/1988 | Kroll | A61B 5/04085 439/77 |

(Continued)

FOREIGN PATENT DOCUMENTS

EP 2 057 943 A1 5/2009

OTHER PUBLICATIONS

Duff "Designing Electronic Systems for EMC;" SciTech Publishing, Raleigh, NC; at pp. 98-110 (2011).*
(Continued)

*Primary Examiner* — Lee S Cohen
*Assistant Examiner* — Erin M Cardinal
(74) *Attorney, Agent, or Firm* — FisherBroyles, LLP

(57) ABSTRACT

An apparatus includes: a first layer including first and second measurement electrodes disposed at a distance from one another, wherein the first and second measurement electrodes are skin electrodes that measure an electric physiological property from a skin; and a second layer disposed on top of the first layer including first and a second shielding elements that are electrically conductive and arranged to cover at least partially both the first and second measurement electrodes to protect the first and second measurement electrode against electromagnetic interference. Each of the shielding elements are connected to a skin electrode. The first shielding element and the second shielding element extend adjacent with respect to one another between the first and second measurement electrodes on a plane defined by the second layer. The second shielding element is electrically isolated from the first shielding element.

14 Claims, 6 Drawing Sheets

(51) Int. Cl.
*H05K 9/00* (2006.01)
*A61B 5/00* (2006.01)
*A61B 5/0245* (2006.01)
*A61B 5/04* (2006.01)
*A61B 5/0424* (2006.01)

(52) U.S. Cl.
CPC ........ *A61B 5/04085* (2013.01); *A61B 5/6831* (2013.01); *H05K 9/0081* (2013.01); *A61B 5/04* (2013.01); *A61B 5/0424* (2013.01); *A61B 2562/164* (2013.01); *A61B 2562/182* (2013.01)

(58) Field of Classification Search
USPC .................................................. 600/388–390
See application file for complete search history.

(56) References Cited

U.S. PATENT DOCUMENTS

| | | | | |
|---|---|---|---|---|
| 6,259,939 | B1* | 7/2001 | Rogel | A61B 5/04085 128/903 |
| 6,453,186 | B1 | 9/2002 | Lovejoy et al. | |
| 7,176,387 | B1* | 2/2007 | Huang | D02G 3/12 174/393 |
| 8,165,654 | B2* | 4/2012 | Tang | A61B 5/0408 600/382 |
| 2002/0026112 | A1* | 2/2002 | Nissila | A61B 5/02438 600/372 |
| 2009/0124881 | A1* | 5/2009 | Rytky | A61B 5/0408 600/388 |
| 2010/0060300 | A1* | 3/2010 | Muller | A61B 5/0408 324/686 |
| 2013/0289376 | A1* | 10/2013 | Lang | A61B 5/0408 600/372 |

OTHER PUBLICATIONS

European Search Report for corresponding European Application No. EP 17 15 4739, 2 pages, dated Jul. 26, 2017.
Extended European Search Report for corresponding European Application No. EP 17 154 739.1, 3 pages, dated Aug. 8, 2017.

* cited by examiner

EMI PROTECTION FOR PHYSIOLOGICAL MEASUREMENTS

CROSS-REFERENCE TO RELATED APPLICATION

This application claims benefit to European Application No. 17154739.1, filed Feb. 6, 2017, which is incorporated by reference herein in its entirety.

BACKGROUND

Field

The present invention relates to a field of physiological or biometric measurements and, in particular, protecting a measurement component against electro-magnetic interference.

Description of the Related Art

Electrodes, signal lines and such components of a measurement circuitry are susceptible to electromagnetic interference (EMI). EMI typically corrupts a measurement signal such as an electrocardiogram or a bioimpedance signal and degrades measurement accuracy. Protection against EMI is advantageous.

SUMMARY

The present invention is defined by the subject matter of the independent claims.

Embodiments are defined in the dependent claims.

BRIEF DESCRIPTION OF THE DRAWINGS

In the following the invention will be described in greater detail by means of preferred embodiments with reference to the attached [accompanying] drawings, in which

FIGS. 3C and 3D illustrate another configuration of the shielding elements of FIGS. 3A and 3B;

DETAILED DESCRIPTION

The following embodiments are exemplifying. Although the specification may refer to "an", "one", or "some" embodiment(s) in several locations of the text, this does not necessarily mean that each reference is made to the same embodiment(s), or that a particular feature only applies to a single embodiment. Single features of different embodiments may also be combined to provide other embodiments.

Figure 1:
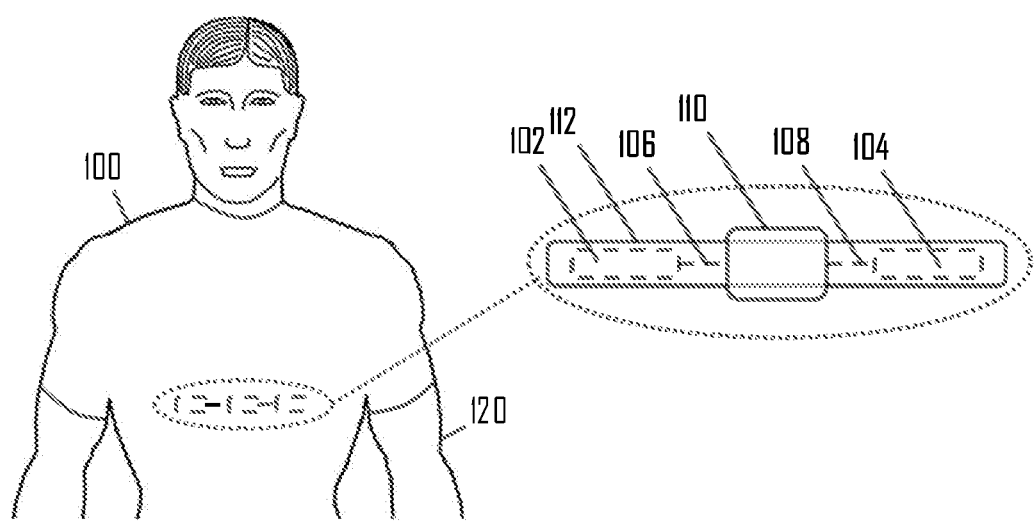
FIG. 1 illustrates an apparel comprising a measurement circuitry.

FIG. 1 illustrates an example of an apparatus to which embodiments of the invention may be applied. The apparatus may comprise a measurement circuitry or a part of a measurement circuitry configured to carry out electric physiological measurements such as measuring an electrocardiogram (ECG), electroencephalographyelectromuography (EMG), amperometry, bioimpedance. The apparatus may comprise a first layer comprising at least a first measurement electrode 102 and a second measurement electrode 104 disposed at a distance from one another, wherein the first measurement electrode 102 and second measurement electrode 104 are skin electrodes configured to measure an electric physiological property from a user's 120 skin. The first layer is also denoted as an electrode layer in the description below. The first layer may be considered as a layer that is designed to contact the skin and it may form a bottom layer of the apparatus. Other layers may be provided on top of the first layer.

In an embodiment, the apparatus is or is comprised in an article of clothing, an apparel, or a garment such as a shirt 100. In another embodiment, the apparatus is or is comprised in a strap or another fixing structure that attaches the measurement electrodes 102, 104 to the skin.

The apparatus may further comprise a signal processing circuitry 110 provided in a casing. The signal processing circuitry 110 may be configured to process electric signals acquired from the skin by the electrodes 102, 104. The signal processing circuitry 110 may comprise a differential amplifier, a filter, an analog-to-digital (A/D) converter, and a digital signal processor. The casing may further house a wireless communication circuitry operating according to Bluetooth specifications, for example. The signal processing circuitry may use the wireless communication circuitry to wirelessly transmit processed measurement signals to another apparatus.

The apparatus may further comprise signal lines 106, 108 that connect the measurement electrodes 102, 104 to the signal processing circuitry 110. The signal processing circuitry 110 may be provided in a casing that has a shielding element against electromagnetic interference (EMI) radiating or induced from one or more sources outside the user's body. The measurement electrodes 102, 104 and the signal lines 106, 108 are, on the other hand, vulnerable to the EMI.

Embodiments of the invention provide the apparatus with a second layer 112 disposed on top of the first layer and comprising: a first shielding element which is electrically conductive and arranged to cover at least partially both the first measurement electrode 102 and second measurement electrode 104 so as to protect the first measurement electrode 102 and second measurement electrode 104 against the EMI, wherein the first shielding element is connected to a skin electrode; and a second shielding element which is electrically conductive, and arranged to cover at least partially both the first measurement electrode 102 and second measurement electrode 104 so as to protect the first measurement electrode 102 and second measurement electrode 104 against the EMI, wherein the second shielding element is connected to a skin electrode different from the skin electrode to which the first shielding element is connected. The first shielding element and the second shielding element extend adjacent with respect to one another between the first measurement electrode 102 and the second measurement electrode 104 on a plane defined by the second layer. The second shielding element is electrically isolated from the first shielding element.

By arranging each of the shielding elements to protect both measurement electrodes 102, 104 and in such a manner that shielding elements extend adjacent with respect to one another between measurement electrodes 102, 104 provides a technical effect where each shielding element absorbs EMI that affects each measurement electrode 102, 104 such that both shielding elements experience the same or similar EMI characteristics. In other words, the shielding elements absorb the EMI in a substantially similar manner. This reduces or eliminates a differential EMI component that could otherwise reach the signal processing circuitry 110. Common mode filtering employed by the signal processing circuitry 110 may then eliminate any residual EMI reaching the signal processing circuitry 110.

On the other hand, isolating the two shielding elements from one another eliminates differential interference components arising from poor or varying skin contacts between the skin electrodes and the skin. The skin contact may vary during an exercise such as running, for example. Since each shielding element is "open-ended" when viewed from the skin electrode towards the shielding element, a signal modulated by electrical charges from the skin (a body potential) cannot cause a current through the shielding element and a differential interference component to the measurement electrodes.

In an embodiment, the skin electrodes ground the EMI absorbed by the shielding elements.

In an embodiment, the shielding elements are arranged at a proximity of both measurement electrodes. The proximity between the shielding element and the measurement electrodes may be defined such that the shielding element is provided so close to the measurement electrodes that it is capable of absorbing EMI that would otherwise be induced to the measurement electrodes. In some embodiments, the shielding element may be arranged on top of the measurement electrodes but, in other embodiments, the shielding element may be arranged at the proximity with the measurement electrodes such that it is not on top of at least one of the measurement electrodes but still close enough to protect the at least one of the measurement electrodes against the EMI.

As disclosed in the embodiments below, the shielding elements extend adjacent with respect to one another between the first measurement electrode 102 and the second measurement electrode such that the shielding elements are arranged to extend in parallel at a section of the second layer that is between the measurement electrodes, when viewed from a top or bottom (see FIGS. 2A, 3A, 4A, 5A). From another perspective, the shielding elements extend adjacent with respect to one another between the first measurement electrode 102 and the second measurement electrode such that the shielding elements are arranged to extend in parallel at a section of the second layer that is between the measurement electrodes, when viewed from a source of the EMI. The source of the EMI is typically outside the user's skin and radiates EMI towards the user's skin to which the apparatus is positioned in use. In use, the first and second layer may be aligned with the skin. In such a case, the source of the EMI may be considered as a point that is at a distance from the plane formed by the skin as well as the first and second layer.

In some applications, it may not be necessary to arrange the shielding elements to extend as adjacent with respect to one another. For example, if the electrodes and the shielding elements are arranged in an apparel and the EMI characteristics are substantially similar in a large area of the apparel, e.g. on a front side of a shirt, the shielding elements may travel between the measurement electrodes via substantially different routes such that they do not extend as adjacent with respect to one another.

Figure 2A:
FIGS. 2A and 2B illustrate an embodiment of shielding elements for providing electromagnetic interference (EMI) shielding for the measurement circuitry.
Figure 2B:
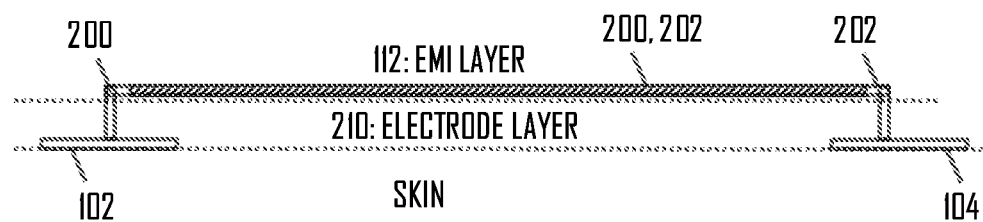

Let us now describe some embodiments for arranging the shielding elements. FIGS. 2A and 2B illustrate an embodiment where the shielding elements 200, 202 are each formed by a signal line forming a loop. The signal line 200 is connected to the measurement electrode 102 at both ends, and the signal line 202 is connected to the measurement electrode 104 at both ends. The signal line 200 may first extend vertically from the first measurement electrode 102 on the electrode layer 210 to the second layer now called an EMI layer 112 and then horizontally from a position of the first measurement electrode 102 towards the second measurement electrode 104. At a proximity of the second measurement electrode 104 or above the second measurement electrode 104, the signal line 200 takes a U-turn and extends back towards the first measurement electrode and, on top of the first measurement electrode 102, the signal line may extend vertically to connect to the first measurement electrode 102 In a similar manner, the signal line 202 may first extend vertically from the second measurement electrode 104 on the electrode layer 210 to the EMI layer 112 and then horizontally, adjacent to the signal line 200, from a position of the second measurement electrode 104 towards the first measurement electrode 102. At a proximity of the first measurement electrode 102 or above the first measurement electrode 102, the signal line 202 takes a U-turn and extends back towards the second measurement electrode and, on top of the second measurement electrode 104, the signal line 202 may extend vertically to connect to the second measurement electrode 104. In this embodiment, the signal lines 200, 202 extend to opposite directions on the same plane defined by the EMI layer 112 as adjacent to one another.

FIG. 2B illustrates a side view of FIG. 2A. A lining indicates an area where the signal lines 200, 202 overlap from this viewpoint. FIG. 2B also illustrates how the signal lines 200, 202 extend vertically between the layers 210, 112 and connect to the respective measurement electrodes 102, 104.

Figure 2C:
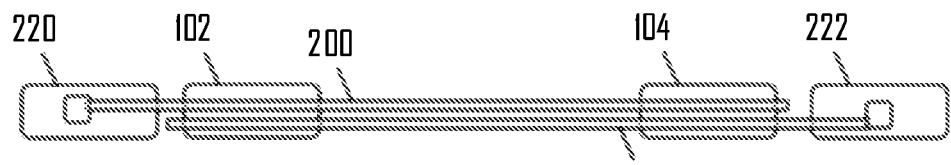
FIGS. 2C and 2D illustrate another configuration of the shielding elements of FIGS. 2A and 2B.
Figure 2D:

In the embodiment of FIGS. 2A and 2B, the shielding elements 200, 202 are connected to the measurement electrodes 102, 104. FIGS. 2C and 2D illustrate an embodiment where the skin electrodes 220, 222 to which the shielding elements 200, 202 connect are other skin electrodes, e.g. grounding electrodes. In this embodiment, the measurement electrodes 102, 104 may be provided such that both shielding elements 200, 202 cover both measurement electrodes 102, 104. For example, the measurement electrodes 102, 104 may be provided between the grounding electrodes 220, 222. In another embodiment, the grounding electrodes 220, 222 are disposed between the measurement electrodes 102, 104, and the shielding elements 200, 202 may extend to over the grounding electrodes 220, 222 to cover the measurement electrodes at least partly. The grounding electrodes 220, 222 may be provided on the electrode layer 210.

Figure 3A:
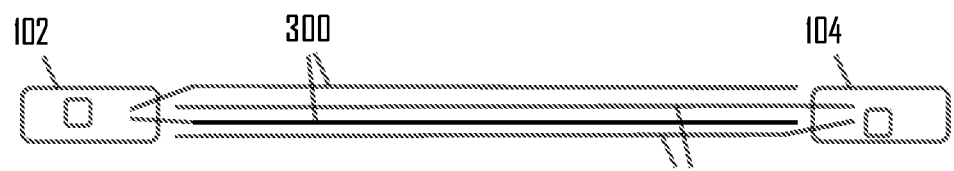
FIGS. 3A to 3D illustrate another embodiment of shielding elements for providing EMI shielding for the measurement circuitry.
Figure 3B:
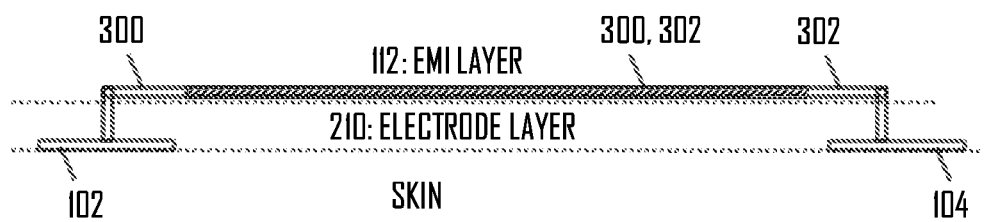

FIGS. 3A to 3D illustrate an embodiment where the shielding elements are formed by open-ended strips or signal lines extending from a skin electrode. Referring to FIGS. 3A and 3B, each shielding element 300, 302 may comprise a plurality of open-ended strips or signal lines extending from a respective measurement electrode 102, 104. The signal lines of the shielding element 300 may extend from the measurement electrode 102 and from the electrode layer 210 to the EMI layer 112 and then on the EMI layer 112 towards the second measurement electrode 104. The signal lines may extend to the proximity of the second measurement electrode 104 or over the second measurement electrode 104 so as to protect both measurement electrodes against the EMI. Similarly, the signal lines of the shielding element 302 may extend from the measurement electrode 104 and from the electrode layer 210 to the EMI layer 112 and then on the EMI layer 112 towards the first measurement electrode 102. The signal lines may extend to the proximity of the first measurement electrode 102 or over the first measurement electrode 102 so as to protect both measurement electrodes against the EMI.

In the embodiment of FIGS. 3A to 3D, the signal lines of the shielding elements 300, 302 are interlaced with respect to one another such that they are arranged in an alternating manner, as illustrated in the top/bottom view of FIG. 3A. The signal lines may be provided in the same plane, as illustrated in the side view of FIG. 3B.

Figure 3C:
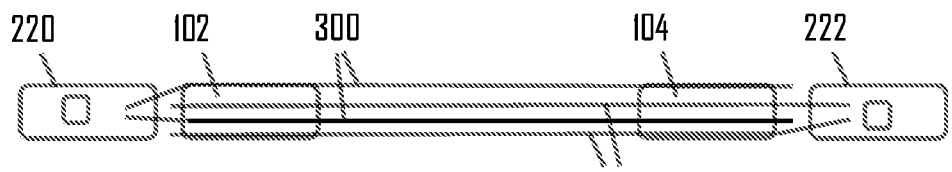
Figure 3D:
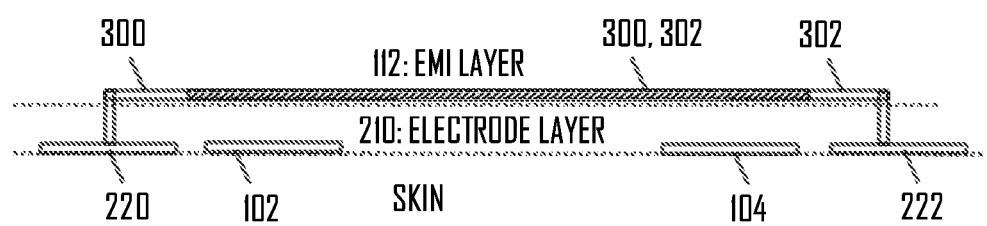

FIGS. 3C and 3D illustrate an embodiment where the shielding elements 300, 302 are connected to the grounding electrodes 220, 222 other than the measurement electrodes 102, 104. In this embodiment, the measurement electrodes 102, 104 may be provided such that both shielding elements 300, 302 cover both measurement electrodes 102, 104. For example, the measurement electrodes 102, 104 may be provided between the grounding electrodes 220, 222. In another embodiment, the grounding electrodes 220, 222 are disposed between the measurement electrodes 102, 104, and the shielding elements 300, 302 may extend to over the grounding electrodes 220, 222 to cover the measurement electrodes at least partly. The grounding electrodes 220, 222 may be provided on the electrode layer 210.

In the embodiment of FIGS. 3A to 3D, the shielding elements are formed by straight signal lines. In another embodiment, the signal lines may form curves or a pattern other than an assembly of straight lines. Each signal line may form a uniform curve.

Figure 4A:
FIGS. 4A and 4B illustrate an embodiment where the EMI shielding is formed by interlacing comb-shaped shielding elements.
Figure 4B:
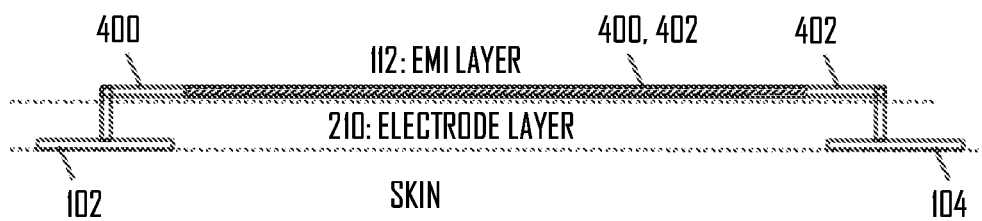

FIGS. 4A to 4D illustrate an embodiment where the shielding elements 400, 402 have a comb-shape. Referring to FIGS. 4A and 4B, a shielding element 400 may connect to the measurement electrode 102 and have a base line that extends from the measurement electrode 102 to the EMI layer 112 and on the EMI layer 112 towards the measurement electrode 104. The base line may extend to the proximity of the measurement electrode 104 or over the measurement electrode 104 to cover the measurement electrode 104. Comb peaks may extend from the base line as perpendicular to the base line and on the plane defined by the EMI layer 112, as illustrated in the top/bottom view of FIG. 4A. In a similar manner, a shielding element 402 may connect to the measurement electrode 104 and have a base line that extends from the measurement electrode 104 to the EMI layer 112 and on the EMI layer 112 towards the measurement electrode 102. The base line may extend to the proximity of the measurement electrode 102 or over the measurement electrode 102 to cover the measurement electrode 102. Comb peaks may extend from the base line as perpendicular to the base line and on the plane defined by the EMI layer 112, as illustrated in the top/bottom view of FIG. 4A.

The comb peaks of the shielding element 400 may extend towards the base line of the shielding element 402, and the comb peaks of the shielding element 400 may extend towards the base line of the shielding element 402, as illustrated in FIG. 4A. The comb peaks and the base lines of the shielding elements may extend in the same plane defined by the EMI layer 112, as illustrated in the side view of FIG. 4B.

In the embodiment of FIGS. 4A to 4D, the comb peaks of the shielding elements 400, 402 are interlaced with respect to one another such that they are arranged in an alternating manner, as illustrated in the top/bottom view of FIG. 4A. In other words, the combs may be facing one another at such proximity that comb peaks of one shielding element are provided between comb peaks of another shielding element.

In the embodiment of FIGS. 4A to 4D, the comb peaks extend perpendicularly from the base line, i.e. the angle between the comb peaks and the base line is 90 degrees. In another embodiment, the angle may be another, e.g. 45 degrees, 135 degrees, or at any angle between 10 and 170 degrees. In an embodiment, the angle may be the same for both shielding elements to enable the interlacing efficiently. In another embodiment, the angles of the peaks with respect to the base lines may be different for the shielding elements 400, 402, and the interlacing may still be achieved, if the spacing between the peaks is sufficiently large. In general, the angle(s) may be arbitrary as long as the comb peaks of the different shielding elements 400, 402 can be interlaced.

Figure 4C:
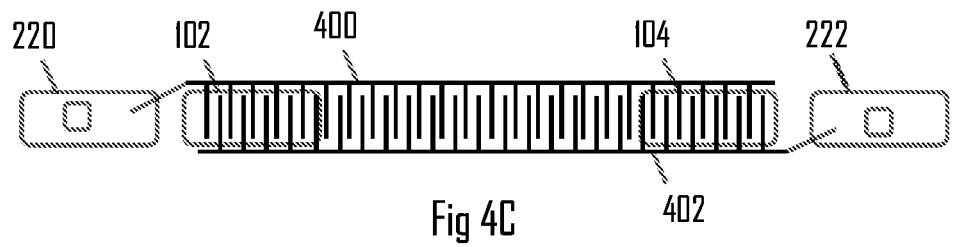
FIGS. 4C and 4D illustrate another configuration of the shielding elements of FIGS. 4A and 4B.
Figure 4D:

FIGS. 4C and 4D illustrate an embodiment where the shielding elements 400, 402 are connected to the grounding electrodes 220, 222 other than the measurement electrodes 102, 104. In this embodiment, the measurement electrodes 102, 104 may be provided such that both shielding elements 400, 402 cover both measurement electrodes 102, 104. For example, the measurement electrodes 102, 104 may be provided between the grounding electrodes 220, 222. In another embodiment, the grounding electrodes 220, 222 are disposed between the measurement electrodes 102, 104, and the shielding elements 400, 402 may extend to over the grounding electrodes 220, 222 to cover the measurement electrodes at least partly. The grounding electrodes 220, 222 may be provided on the electrode layer 210.

In the embodiments of FIGS. 2A to 4D, the shielding elements are disposed symmetrically with respect to one another such that the axis of symmetry is an axis that extends between the shielding elements and between the skin electrodes, when viewed from the top/bottom.

Figure 5A:
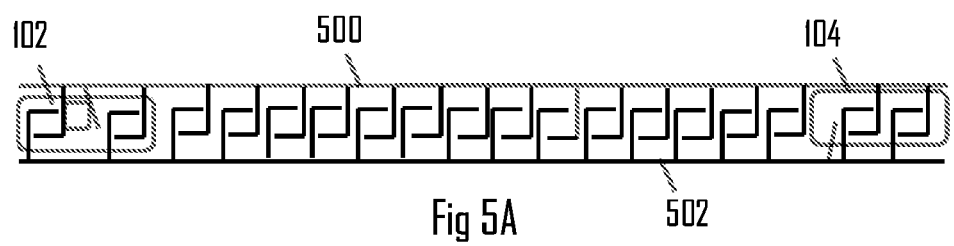
FIGS. 5A and 5B illustrate an embodiment where the EMI shielding is formed by intertwining hook-shaped shielding elements.
Figure 5B:
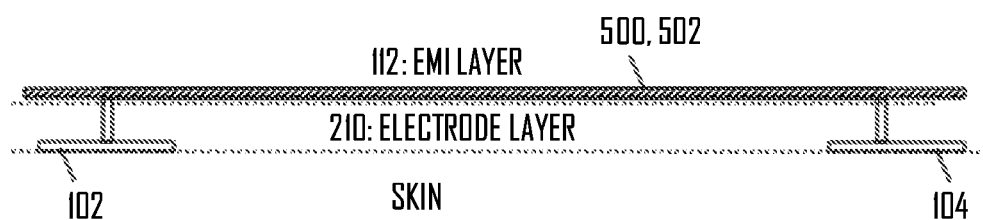

FIGS. 5A to 5D illustrate an embodiment where the shielding elements 400, 402 have a hook-shape. Referring to FIGS. 5A and 5B, a shielding element 500 may connect to the measurement electrode 102 and have a base line that extends from the measurement electrode 102 to the EMI layer 112 and on the EMI layer 112 towards the measurement electrode 104. The base line may extend to the proximity of the measurement electrode 104 or over the measurement electrode 104 to cover the measurement electrode 104. Hook-shaped signal lines may extend from the base line on the plane defined by the EMI layer 112, as illustrated in the top/bottom view of FIG. 4A. In a similar manner, a shielding element 502 may connect to the measurement electrode 104 and have a base line that extends from the measurement electrode 104 to the EMI layer 112 and on the EMI layer 112 towards the measurement electrode 102. The base line may extend to the proximity of the measurement electrode 102 or over the measurement electrode 102 to cover the measurement electrode 102. Hook-shaped signal lines may extend from the base line on the plane defined by the EMI layer 112, as illustrated in the top/bottom view of FIG. 5A.

The hooks of the shielding element 500 may extend towards the base line of the shielding element 502, and the hooks of the shielding element 502 may extend towards the base line of the shielding element 500. The hooks of the shielding element 500 may intertwine with hooks of the shielding element 502 without connecting one another, as illustrated in FIG. 5A. The shielding elements 500, 502 may have the same form and the same dimensions, and they may be arranged such that the hooks intertwine in the illustrated manner.

Figure 5C:
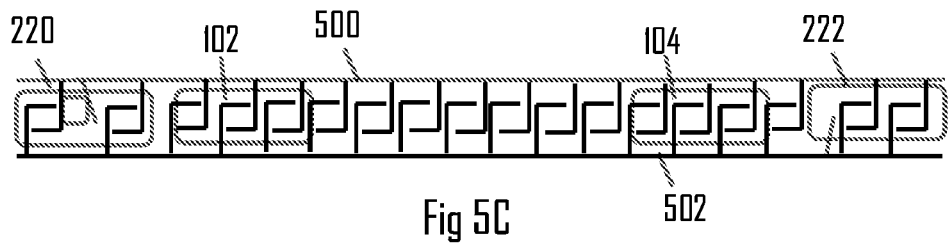
FIGS. 5C and 5D illustrate another configuration of the shielding element of FIGS. 5A and 5B.
Figure 5D:

FIGS. 5C and 5D illustrate an embodiment where the shielding elements 500, 502 are connected to the grounding electrodes 220, 222 other than the measurement electrodes 102, 104. In this embodiment, the measurement electrodes 102, 104 may be provided such that both shielding elements 500, 502 cover both measurement electrodes 102, 104. For example, the measurement electrodes 102, 104 may be provided between the grounding electrodes 220, 222. In another embodiment, the grounding electrodes 220, 222 are disposed between the measurement electrodes 102, 104, and the shielding elements 500, 502 may extend to over the grounding electrodes 220, 222 to cover the measurement electrodes at least partly. The grounding electrodes 220, 222 may be provided on the electrode layer 210.

Figure 6:
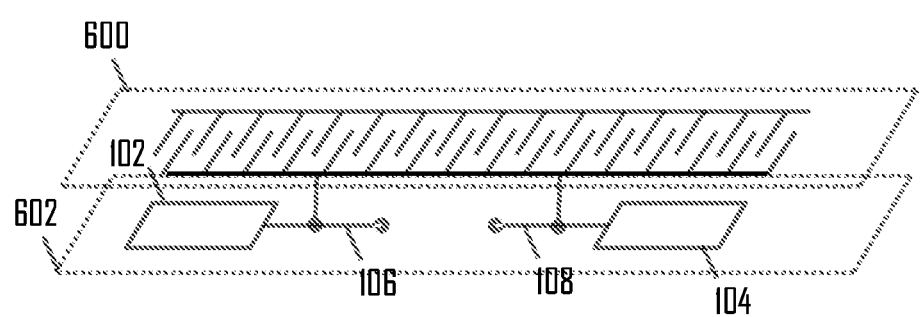
FIG. 6 illustrates a perspective view of an embodiment of the comb-shaped shielding elements.

Let us now elaborate the positioning of the shielding elements of the above-described embodiments on a general level with reference to FIG. 6. FIG. 6 illustrates a perspective view of the embodiment of FIGS. 4A and 4B where the comb-shaped shielding elements extend to cover the measurement electrodes 102, 104. The shielding elements may be connected to the measurement electrodes 102, 104 through signal lines 106, 108 that connect the measurement electrodes 102, 104 to the signal processing circuitry 110, for example. As illustrated in FIG. 6, the electrode layer 210 comprising the measurement electrodes 102, 104 defines a first plane 602 that substantially conforms with the skin when the apparatus is in use and attached to the user. On top of the first plane, the EMI layer 112 comprising the shielding elements defines a second plane 600 that substantially conforms to the first plane and, the skin when the apparatus is in use.

In the embodiments of FIGS. 2A to 3D, the shielding elements are configured to extend as adjacent with respect to one another in only one dimension of the second plane 600.

In the embodiments of FIGS. 4A to 5D, the shielding elements are configured to extend as adjacent with respect to one another in two dimensions of the second plane 600.

Figure 7:
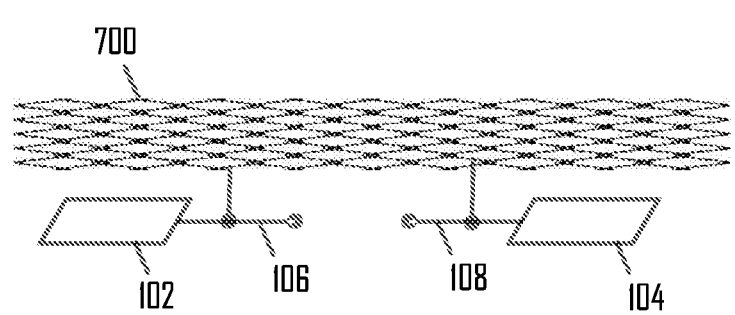
FIG. 7 illustrates an embodiment where the EMI shielding elements form a mesh structure.

In the embodiment of FIG. 7, the EMI layer 112 is a mesh layer 700 where the shielding elements are configured to intertwine in three dimensions to form a mesh structure. As in other embodiments, the shielding elements may be isolated from one another and connect to different electrodes, e.g. the measurement electrodes 102, 104 or the grounding electrodes 220, 222.

In an embodiment, an electromagnetic absorption area covered by the first shielding element towards a source of the electromagnetic interference is substantially equal to an electromagnetic absorption area covered by the second shielding element towards a source of the electromagnetic interference. This provides a technical effect that the shielding elements are capable of absorbing a substantially equal amount of EMI, thus reducing differential mode interference.

In an embodiment, the first shielding element is arranged in a symmetric manner with respect to the second shielding element. In an embodiment, the first shielding element extends from a position (on top) of the first measurement electrode towards the second measurement electrode in an identical manner as the second shielding element extends from a position (on top) of the second measurement electrode towards the first measurement electrode.

In general, the shielding elements may be arranged to protect the measurement electrodes 102, 104 such that they both experience a substantially identical electromagnetic interference field. This may be achieved by arranging the shielding elements to extend as adjacent to one another, providing the shielding elements with the same absorption area towards the source of the EMI, and/or arranging the shielding elements in a symmetric manner.

In all embodiment described above, the number of shielding elements is two but the number of shielding elements may be higher than two, and the number of shielding elements may be computed as how many shielding elements are isolated from one another.

Figure 8:
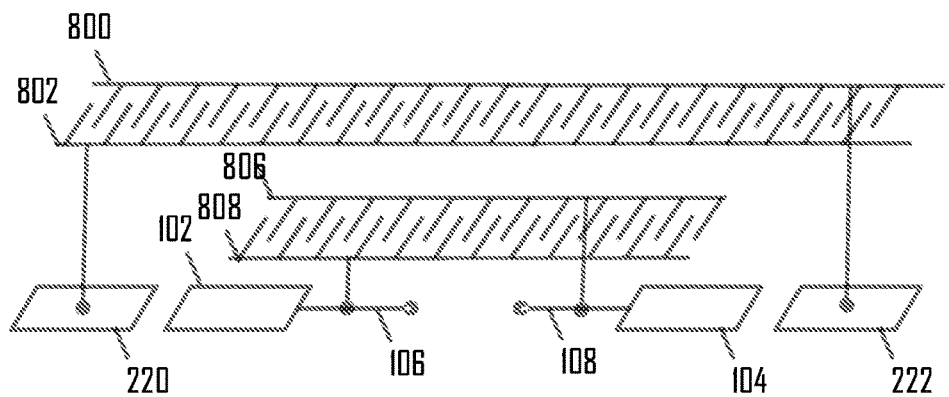
FIG. 8 illustrates an embodiment where two layers of EMI shielding is provided.

FIG. 8 illustrates an embodiment which combines the embodiments of FIGS. 4A/B and 4C/D. As illustrated in FIG. 8, the EMI layer 112 may comprise at least two sub-layers, each sub-layer comprising an EMI shield provided by at least two shielding elements. Referring to FIG. 8, a first sub-layer may be provided on top of the electrode layer 210 and it may comprise a first shielding element 806 which is electrically conductive and arranged at a proximity of both the first measurement electrode 102 and second measurement electrode 104 so as to protect the first measurement electrode 102 and second measurement electrode 104 against electromagnetic interference, wherein the first shielding element is connected to a skin electrode (the measurement electrode 104 in this example). The first sub-layer may further comprise a second shielding element 808 which is electrically conductive, and arranged at a proximity of both the first measurement electrode 102 and second measurement electrode 104 so as to protect the first measurement electrode 102 and second measurement electrode 104 against the electromagnetic interference, wherein the second shielding element is connected to a skin electrode different from the skin electrode to which the first shielding element is connected (the measurement electrode 102 in this example). The first and second shielding element extend adjacent with respect to one another between the measurement electrodes 102, 104 on a plane defined by the first sub-layer.

On top of the first sub-layer, there is provided a second sub-layer that comprises a third shielding element 800 which is electrically conductive and arranged at a proximity of both the first measurement electrode 102 and second measurement electrode 104 so as to protect the first measurement electrode 102 and second measurement electrode 104 against electromagnetic interference, wherein the third shielding element is connected to a skin electrode (the grounding electrode 220 in this example). The second sub-layer may further comprise a fourth shielding element 802 which is electrically conductive, and arranged at a proximity of both the first measurement electrode 102 and second measurement electrode 104 so as to protect the first measurement electrode 102 and second measurement electrode 104 against the electromagnetic interference, wherein the fourth shielding element is connected to a skin electrode different from the skin electrodes to which the other shielding elements are connected (the grounding electrode 222 in this example). The third and fourth shielding element 800, 802 extend adjacent with respect to one another between the measurement electrodes 102, 104 on a plane defined by the second sub-layer on top of the plane defined by the first sub-layer.

FIG. 8 illustrates an embodiment where the shielding elements 800 to 808 have the comb-shaped form, but the shape of the shielding elements may be any one of the other embodiments described herein, e.g. any one of FIGS. 2A, 3A, and 5A, or another shape.

In another embodiment, the shielding elements 806, 808 are connected to the respective grounding electrodes 220, 222 while the shielding elements 800, 802 are connected to the respective measurement electrodes 102, 104. In another embodiment, all the shielding elements 800 to 808 are connected to different grounding electrodes.

In an embodiment, a substrate layer may be provided between the electrode layer and the EMI layer. The electrodes may be attached to the substrate on a side that contacts the skin, and the EMI layer may be provided on an opposite side of the substrate. The substrate layer may be a textile layer, for example.

In the embodiments described above, the shielding elements may be produced by using one of the following techniques: conductive threading stitched or sewn on top of the electrode layer, conductive fabric weaved on top of the electrode layer, conductive plastic attached on top of the electrode layer, conductive ink printed on top of the electrode layer, or printed electronics printed on top of the electrode layer.

Figure 9:
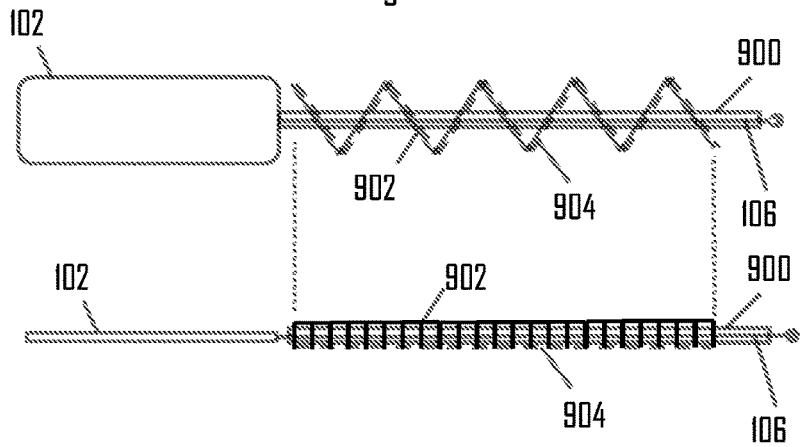
FIG. 9 illustrates an embodiment for providing EMI shielding for a signal line in the form of stitched EMI thread.
Figure 10:
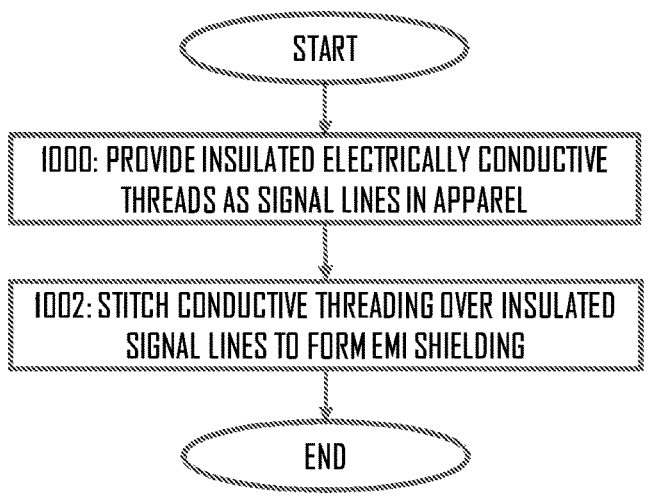
FIG. 10 illustrates a process for producing the EMI shielding of FIG. 9 according to an embodiment of the invention.

FIGS. 9 and 10 relate to embodiments where the EMI shielding is provided for the signal lines 106, 108 of the apparatus. The apparatus according to these embodiments may thus comprise any signal lines that conduct electric signals and are susceptible to the EMI. Referring to FIG. 9, the signal line 106 may comprise an electric conductor that may be formed by an electrically conductive thread or threading in an article of clothing, an apparel or a garment. The electric conductor may be isolated by an isolation layer 900 protecting the electric conductor and isolating the electric conductor. On top of the electric conductor, the EMI shielding may be provided by arranging a conductive threading to cover the electric conductor. The conductive threading may be arranged on top of the electric conductor by stitching or sewing the conductive threading with a sewing machine. The conductive threading may be formed by using zigzag stitching such that the zigzag pattern covers the signal line without penetrating the isolation layer 900. The conductive threading may be sewn through a substrate in which the signal line 106 is provided, e.g. a textile or a garment. When used in an application where the substrate is in contact with the user's skin, the conductive threading thus engages the user's skin and operates as a skin electrode for grounding the EMI.

FIG. 9 illustrates both a top view and a side view of the threading. The top view illustrates that both the threading 902 on top of the substrate and a bobbin threading 904 form the zigzag pattern, the top threading travelling in parallel and on top of the bobbin threading. The side view illustrates how the two threadings 902, 904 intertwine through the substrate and around the signal line 902.

In an embodiment, only the threading 902 forming a pattern on top of the substrate in the sewing process is conductive. In an embodiment, all threading included in the sewing process is conductive, including bobbin threading 904. Accordingly, the threadings 902, 904 together surround the signal line, thus shielding the signal line against the EMI from all directions. The conductive threadings 902, 904 may form a caging such as a Faraday cage for the signal line 106. In such an embodiment, stitches of the threadings 902, 904 may or ground to or contact with the user's skin in use. In an embodiment where the garment comprising the signal line and the stitched threadings 902, 904 is not arranged to contact the user's skin, separate grounding points may be arranged to ground the conductive threading(s) 902, 904.

FIG. 10 illustrates a process for producing the EMI shielding of FIG. 9 described above. Referring to FIG. 10, the process comprises arranging at least one insulated conductive threading as a signal line in an apparel (block 1000). In block 1002, another conductive threading is stitched or sewn over the insulated signal lines to form the EMI shielding. By using the conductive threading stitched over the signal line, the EMI shielding may be provided in an inconspicuous manner and still produced by using conventional means used in textile industry. No separate industrial process is required to generate the EMI layer on top of the signal line.

It will be obvious to a person skilled in the art that, as the technology advances, the inventive concept can be implemented in various ways. The invention and its embodiments are not limited to the examples described above but may vary within the scope of the claims.

The invention claimed is:

1. An apparatus comprising:
a first layer comprising at least a first measurement electrode and a second measurement electrode disposed at a distance from one another, wherein the first measurement electrode and the second measurement electrode are skin electrodes configured to measure an electric physiological property from a skin; and
a second layer disposed in a plane on top of the first layer, the second layer comprising:
a first shielding element which is electrically conductive and arranged to cover at least partially both the first measurement electrode and the second measurement electrode so as to protect the first measurement electrode and the second measurement electrode against electromagnetic interference that is not parallel to the plane of the second layer, wherein the first shielding element is connected to a skin electrode; and
a second shielding element which is electrically conductive, and arranged to cover at least partially both the first measurement electrode and the second measurement electrode so as to protect the first measurement electrode and the second measurement electrode against electromagnetic interference, wherein the second shielding element is connected to a skin electrode different from the skin electrode to which the first shielding element is connected, wherein the first shielding element and the second shielding element extend adjacent with respect to one another between the first measurement electrode and the second measurement electrode on the plane of the second layer that does not contain the first layer, and wherein the second shielding element is electrically isolated from the first shielding element.

2. The apparatus of claim 1, wherein the first shielding element and the second shielding element are configured to extend as adjacent with respect to one another in only one dimension of the plane of the second layer.

3. The apparatus of claim 1, wherein the first shielding element and the second shielding element are configured to extend as adjacent with respect to one another in two dimensions of the plane of the second layer.

4. The apparatus of claim 1, wherein the second layer is a mesh layer where the first shielding element and the second shielding element are configured to intertwine in three dimensions.

5. The apparatus of claim 1, wherein each of the first shielding element and the second shielding element forms a comb structure where comb peaks of the different shielding elements are interlaced.

6. The apparatus of claim 1, wherein an electromagnetic absorption area covered by the first shielding element towards the source of the electromagnetic interference is substantially equal to an electromagnetic absorption area covered by the second shielding element towards the source of the electromagnetic interference.

7. The apparatus of claim 1, wherein the first shielding element is arranged in a symmetric manner with respect to the second shielding element.

8. The apparatus of claim 7, wherein the first shielding element extends from a position of the first measurement electrode towards the second measurement electrode in an identical manner as the second shielding element extends from a position of the second measurement electrode towards the first measurement electrode.

9. The apparatus of claim 1, wherein the first shielding element and the second shielding element are arranged such that they both experience a substantially identical electromagnetic interference field.

10. The apparatus of claim 1, wherein each of the skin electrodes to which the first shielding element and the second shielding element are connected is not a measurement electrode.

11. The apparatus of claim 1, wherein the skin electrode to which the first shielding element is connected is the first measurement electrode, and the skin electrode to which the second shielding element is connected is the second measurement electrode.

12. The apparatus of claim 1, further comprising a third layer disposed on top of the second layer or between the first layer and the second layer, comprising:
a third shielding element which is electrically conductive and arranged at a proximity of both the first measurement electrode and the second measurement electrode so as to protect the first measurement electrode and the second measurement electrode against the electromagnetic interference, wherein the third shielding element is connected to a skin electrode; and
a fourth shielding element which is electrically conductive, and arranged at a proximity of both the first measurement electrode and the second measurement electrode so as to protect the first measurement electrode and the second measurement electrode against the electromagnetic interference, wherein the fourth shielding element is connected to a skin electrode different from the skin electrode to which the third shielding element is connected,
wherein the third shielding element and the fourth shielding element extend adjacent with respect to one another between the first measurement electrode and the second measurement electrode on the plane of the second layer, and wherein all the shielding elements are electrically isolated from one another, and
wherein the first shielding element is connected to the first measurement electrode and the second shielding element is connected to the second measurement electrode, and wherein at least one of the skin electrode to which the third shielding element is connected and the skin electrode to which the fourth shielding element is connected is a measurement electrode.

13. The apparatus of claim 1, further comprising a third layer disposed on top of the second layer or between the first layer and the second layer, comprising:
a third shielding element which is electrically conductive and arranged at a proximity of both the first measurement electrode and the second measurement electrode so as to protect the first measurement electrode and the second measurement electrode against the electromagnetic interference, wherein the third shielding element is connected to a skin electrode; and
a fourth shielding element which is electrically conductive, and arranged at a proximity of both the first measurement electrode and the second measurement electrode so as to protect the first measurement electrode and the second measurement electrode against the electromagnetic interference, wherein the fourth shielding element is connected to a skin electrode different from the skin electrode to which the third shielding element is connected,
wherein the third shielding element and the fourth shielding element extend adjacent with respect to one another between the first measurement electrode and the second measurement electrode on the plane of the second layer, and wherein all the shielding elements are electrically isolated from one another, and
wherein the first shielding element is connected to the first measurement electrode and the second shielding element is connected to the second measurement electrode, and wherein the skin electrode to which the third shielding element is connected is not a measurement electrode and the skin electrode to which the fourth shielding element is connected is not a measurement electrode.

14. The apparatus of claim 1, wherein the first and second layers are comprised in an article of clothing.

* * * * *